United States Patent [19]
Hanna

[11] Patent Number: 5,152,786
[45] Date of Patent: Oct. 6, 1992

[54] LENSE FOR KERATOMETRY AND KERATOTOME MORE PARTICULARLY FOR MAKING AN INCISION FOR RECEIVING SUCH A LENSE

[76] Inventor: Khalil Hanna, 19 rue Las-Cases, 75007 Paris, France

[21] Appl. No.: 541,738

[22] Filed: Jun. 21, 1990

[30] Foreign Application Priority Data

Jun. 23, 1989 [FR] France .................. 89 08377

[51] Int. Cl.$^5$ .................. A61F 2/14; A61F 9/00; A61B 17/32
[52] U.S. Cl. .................. 623/5; 606/166; 606/180
[58] Field of Search .............. 606/107, 161, 166, 180; 623/6, 5, 4

[56] References Cited

U.S. PATENT DOCUMENTS

| | | | |
|---|---|---|---|
| 2,754,520 | 7/1956 | Crawford, Jr. .................. | 623/5 |
| 4,715,858 | 12/1987 | Lindstrom .................. | 623/5 |
| 4,810,082 | 3/1989 | Abel, Jr. .................. | 623/5 X |
| 4,842,599 | 6/1989 | Bronstein .................. | 623/5 |
| 4,923,467 | 5/1990 | Thompson .................. | 623/5 |

FOREIGN PATENT DOCUMENTS 0308077 3/1989 European Pat. Off. .................. 623/5

Primary Examiner—Ronald Frinks
Attorney, Agent, or Firm—Pollock, Vande Sande & Priddy

[57] ABSTRACT

A lense for keratometry and a keratotome for making an incision for receiving such a lense. The lense comprises an optical zone and an anchoring zone with a sloping shape such that this zone can be inserted under a strip disengaged from the cornea of the receiving eyeball via a tapering incision diverging from the cornea. The keratotome according to the invention is adapted to perform such an incision. The result is that the lense is anchored in the cornea in a more efficient, less traumatic and more aesthetic manner.

20 Claims, 4 Drawing Sheets

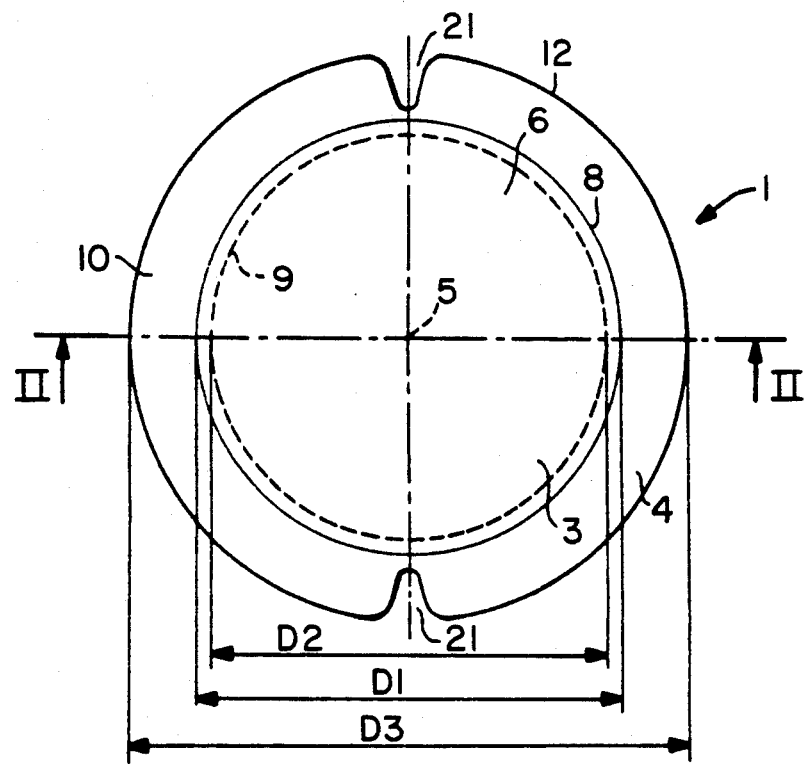
FIG_1
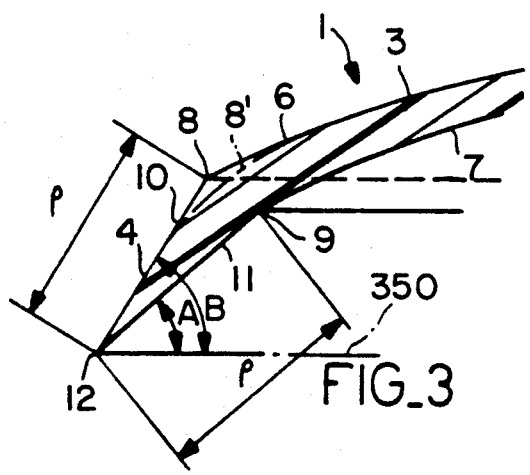
FIG_3
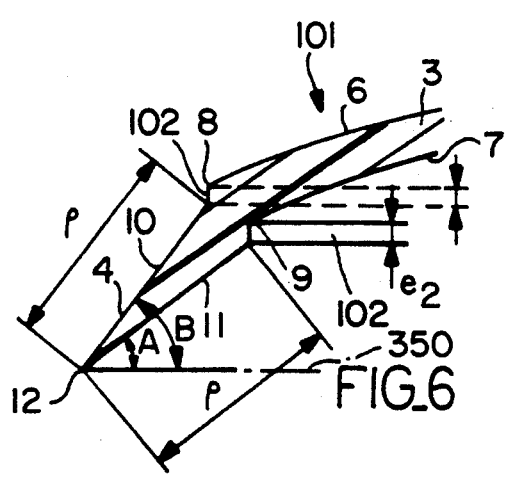
FIG_6
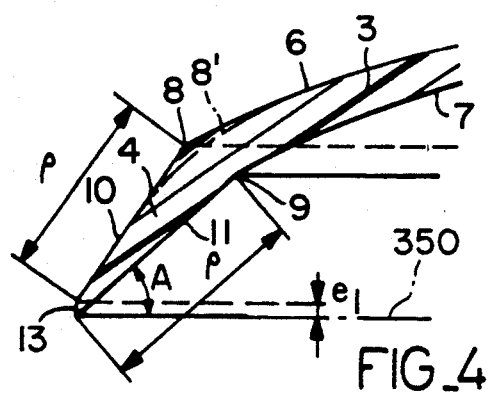
FIG_4
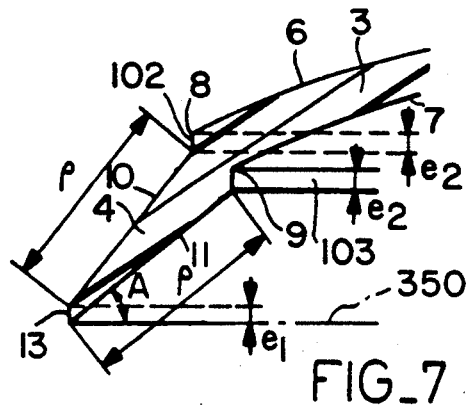
FIG_7

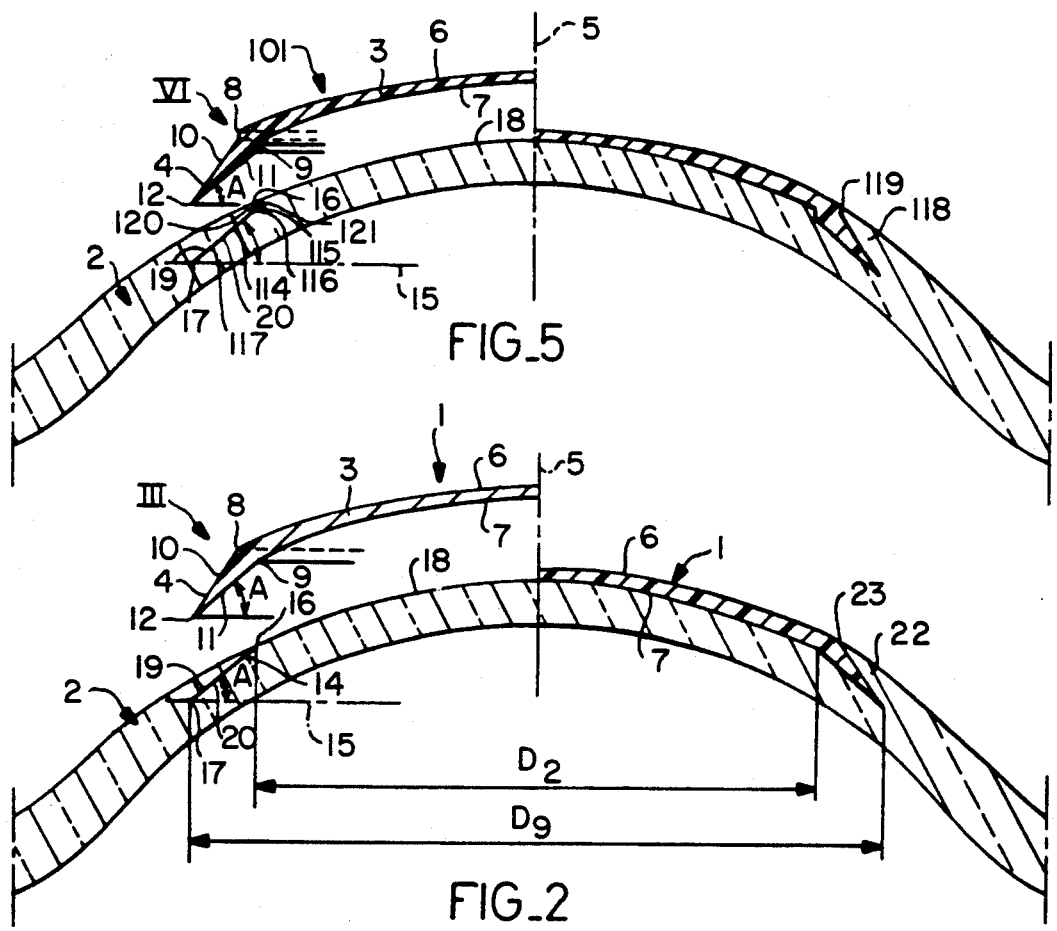

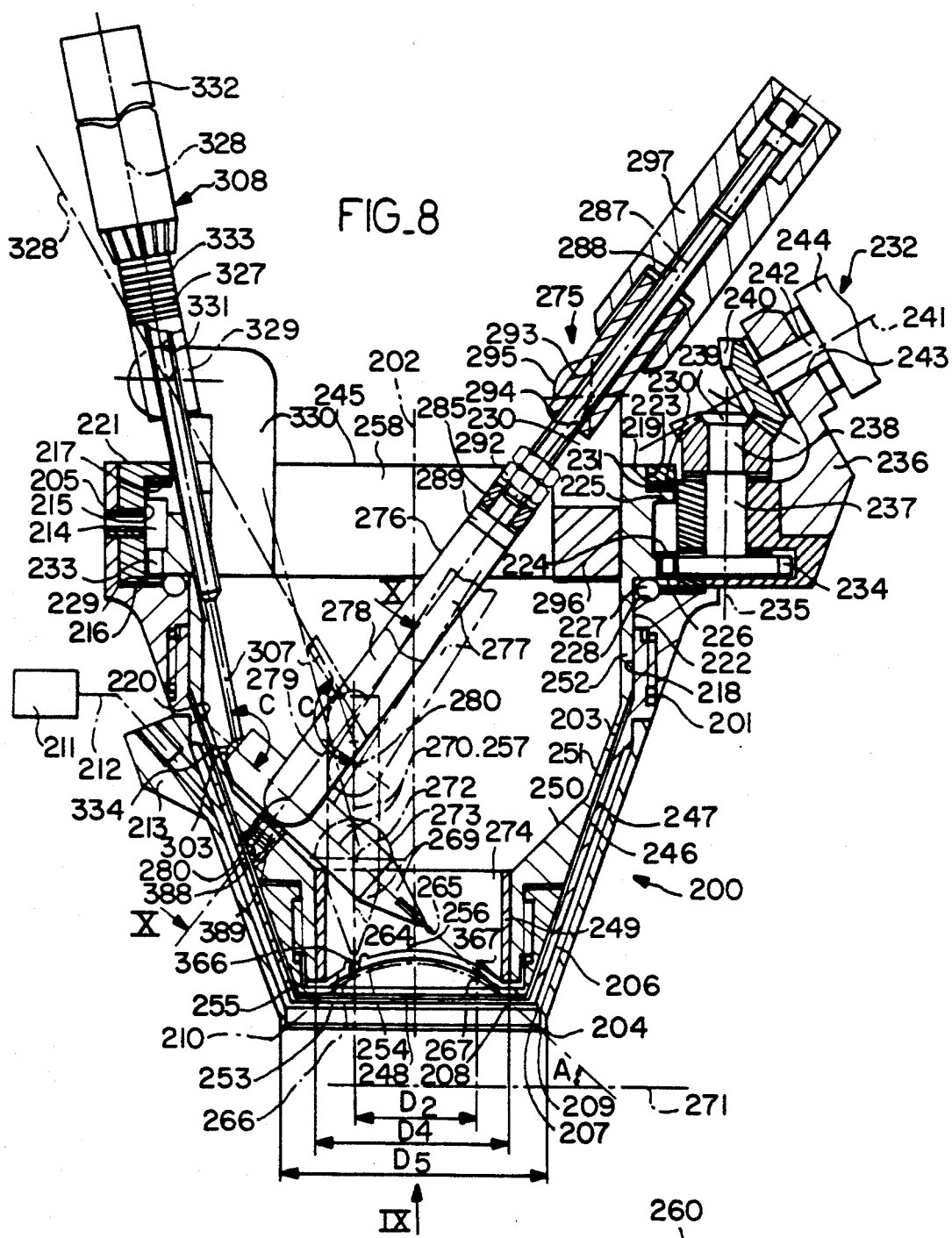
FIG_8
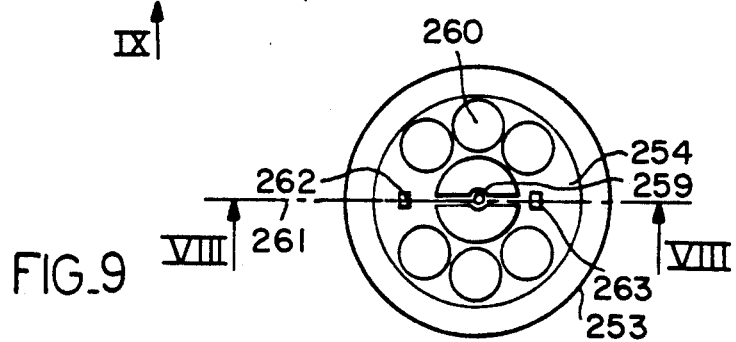
FIG_9

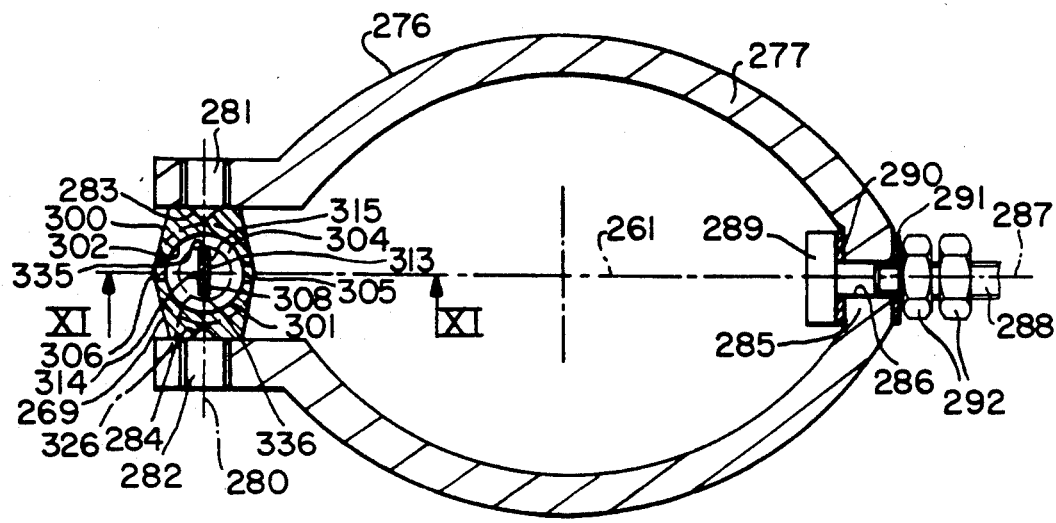
FIG_10
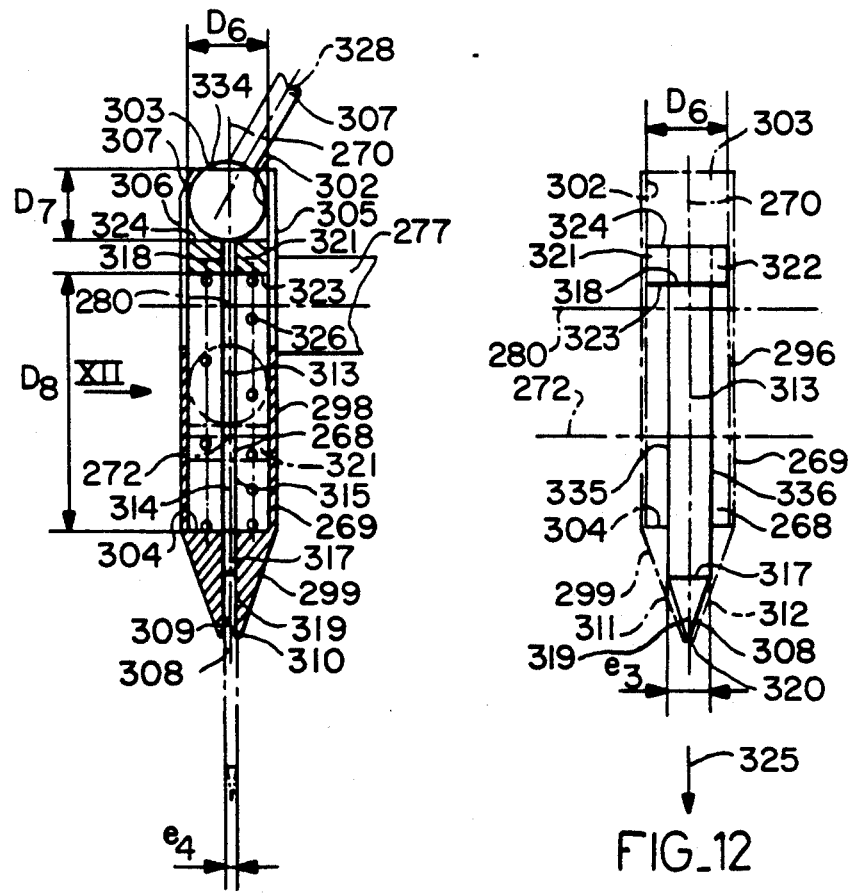
FIG_11  FIG_12

LENSE FOR KERATOMETRY AND KERATOTOME MORE PARTICULARLY FOR MAKING AN INCISION FOR RECEIVING SUCH A LENSE

FIELD OF THE INVENTION

The present invention relates to a lense for use in keratometry, and to a keratotome more particularly adapted for making an incision for receiving such a lense.

BACKGROUND OF THE INVENTION

Keratometry is a technique for correcting ametropy in an eyeball and consists in attaching to the outside of the cornea a corrective lense which was hitherto obtained by removing a cornea from a donor eyeball and processing the cornea to form therein:

an optical zone which has a lenticular shape of predetermined optical axis and is bounded by a convex front face and a concave rear face respectively having respective geometries determined on the one hand in relation to the possibility of applying the rear face of the optical zone closely against the cornea of the eyeball to be corrected (receiving eyeball), more particularly with coincidence between the optical axis and the visual axis of the receiving eyeball, and also in relation to predetermined optical characteristics in dependence on the correction to be applied to said eyeball, and an anchoring zone having an annular shape of revolution around the optical axis and edging the optical zone in the direction away from the optical axis, for insertion into an annular incision in the cornea of the receiving eyeball.

In the prior art techniques the anchoring zone is very thick at the periphery of the lense and its insertion in the incision in the cornea of the receiving eyeball requires a deep incision parallel with the visual axis, and then a deep dissection parallel with the surface of the cornea. This is traumatic and moreover does not ensure the stable anchorage of the lense without a suture, except if the anchoring zone is large; moreover, the considerable thickness of the anchoring zone at the periphery of the lense causes, after its insertion in the cornea, a fillet of excess thickness in relation to the optical zone, and whatever care may be devoted to the production of the lense, i.e., the cutting of the cornea taken from the donor eyeball, it is practically impossible to obtain a regular transition between the lense and the cornea of the receiving eyeball on the surface and in depth around the lense. Moreover, at the surface the epithelium may increase in thickness and modify refraction, which makes this technique imprecise, as does possible mechanical distortion of the lense on insertion.

SUMMARY OF THE INVENTION

It is an object of the invention to improve the known technique of keratometry, more particularly by providing a more satisfactory shaping of the anchoring zone of the lense, so as to improve the transition to the cornea, more particularly on the surface, and to reduce distortion of the lense, whether the lense is produced by the cutting of a cornea coming from a donor eyeball, or directly by molding followed by machining of a flexible biocompatible natural or synthetic polymer or copolymer. The invention also provides a keratotome particularly adapted for making an incision suitable for receiving such an anchoring zone.

The lense for keratometry according to the invention, comprising:

an optical zone which has a lenticular shape of predetermined optical axis and is bounded by a convex front face and a concave rear face whose respective geometries are determined both in relation to the possibility of applying the rear face of the optical zone closely fitting against a cornea, and in relation to predetermined optical characteristics, and an anchoring zone having an annular shape of revolution around the optical axis and edging the optical zone in the direction away from the optical axis for insertion into an annular incision in the cornea, is characterized in that the anchoring zone is disposed rearwardly of the front face of the optical zone and projecting outwardly from the rear face of the optical zone, and the anchoring zone is bounded by a front face and a rear face which are respectively connected to the front face and rear face of the optical zone and converge in the direction away from the optical axis so as to produce a progressive thinning of the anchoring zone from the optical zone as far as a peripheral edge of the lense.

Typically, with reference to a plane perpendicular to the optical axis, the front face of the anchoring zone is inclined substantially less than 90°, and preferably between about 50° and about 55°, while the rear face of the anchoring zone is inclined preferably between about 40° and about 45°, more particularly 42°.

Preferably, the front face and the rear face of the anchoring zone have substantially the same shape and the same dimensions when they are viewed in section along any half-plane bounded by the optical axis.

The anchoring zone thus designed forms around the optical zone a sloping edge which can be inserted into an incision made, in the form of an annular slot of suitable orientation, in the cornea of the receiving eyeball and fitted with precision behind a strip of cornea disengaged by such incision, said strip closely engaging with the front face of the anchoring zone via one of the flanks of the incision, while the other flank of the incision engages tightly with the rear face of the anchoring zone, on condition that the incision has been correctly dimensioned, in a manner which can readily be determined in relation to the geometrical characteristics of the lense. The insertion can be facilitated by making in the anchoring zone at least one notch opening into the peripheral edge of the lense and into zones of the front and rear faces of the anchoring zone which are close to the peripheral edge of the lense. This enables the anchoring zone to be inserted into the incision by a movement comparable to a screwing movement.

The fact that the anchoring zone is tightly inserted into the incision produces an improved regularity of the surface and prevents any pockets in the transition between the cornea of the receiving eyeball and the lense, something which prevents the subsequent formation of any fillet resulting from an increase in epithelium thickness.

Moreover, the incision required for positioning the anchoring zone of the lense according to the invention is not very traumatic in itself, since it involves no removal of cornea material and, as a result of a general inclination, in relation to the visual axis of the receiving eyeball, adapted to a general inclination of the anchoring zone with respect to the optical axis of the optical zone of the lense, it is introduced into the cornea in the direction away from visual axis, i.e., towards relatively thicker zones of the cornea. Consequently, the insertion of the anchoring zone of the lense in said incision itself causes only slightly traumatic deformations of the cornea, so that the use of a lense according to the invention offers maximum guarantees as regards an implantation which is effective and stable over time.

For facilitating the making of the incision, the front and rear faces of the anchoring zone are preferably truncated faces of revolution around the optical axis, but other shapes could also be adopted, such as approximately truncated shapes rounded off at the connection with the front or rear face, respectively, of the optical zone, to ensure a smooth transition.

Similarly, although for geometrical reasons it is preferable that the front and rear faces of the anchoring zone be connected directly to one another and also to the front and rear faces of the optical zone, respectively, for practical reasons it is acceptable for said connections to be made respectively via the intermediary of a peripheral, for example cylindrical, face of revolution around the optical axis, by a peripheral, for example cylindrical, discontinuity, of the front face of the optical zone, of revolution around the optical axis, and by a peripheral, for example cylindrical, shoulder, of the rear face of the optical zone, of revolution around the optical axis. Providing a mutual connection of the front and rear faces of the anchoring zone via a peripheral face of revolution around the optical axis makes it easier to produce the lense and prevent damage to its periphery during manipulations; providing a shoulder at the connection of the rear face of the optical zone to the rear face of the anchoring zone and, jointly or not, a disengagement at the connection of the front face of the optical zone to the rear face of the anchoring zone, may facilitate the design and manufacture of the lense when respectively the rear or front face of the optical zone has a shape differing from a shape of revolution around the optical axis, i.e., in practice a toric shape, with a view to correcting astigmatism in the receiving eyeball. This method of connection can also be selected in other cases, to the extent that it results in greater facility and greater precision of incision of the cornea of the receiving eyeball with a view to the insertion of the anchoring zone of the lense.

The fact is that it is easier and more accurate to start the incision in the cornea of the receiving eyeball by the penetration of a blade parallel with the visual axis, then continuing the incision at an angle in relation to the visual axis, rather than to take action on the cornea of the receiving eyeball at an angle to the visual axis from the start. Clearly, to this end the peripheral shoulder of the rear face of the optical zone of the lense and the peripheral discontinuity of the rear face of the optical zone are adapted to fit tightly to the zones of the flanks of the incision corresponding to its start, parallel with the visual axis, with which the optical axis of the optical zone is caused to coincide when the lense according to the invention is put in place.

However, it is preferable to limit to the minimum necessary the dimensions of this start of the incision parallel with the visual axis, i.e., the dimensions which must be given parallel with the optical axis to the discontinuity of the rear face of the optical zone of the lense and to the shoulder of its rear face, just as it is appropriate to limit the dimensions parallel with the optical axis of the peripheral face possibly provided at the connection of the front and rear faces of the anchoring zone of the lense to one another. Preferably these dimensions are limited to a maximum of the order of 50 $\mu\mu m$; the other dimensions of the lense can readily be determined by those skilled in the art in accordance with the dimensions of the cornea of the receiving eyeball.

In connection with the aforementioned preferred method of incision, in which the cornea of the receiving eyeball is first cut into parallel with the visual axis thereof before the incision is given an inclination suitable for allowing the insertion and retention of the anchoring zone of the lense, the invention provides a keratotome for making an annular incision in a cornea, and comprising to this end:

an outer tubular support forming an envelope, having a predetermined axis and comprising for its application to a cornea, an annular base portion of revolution around the axis of the support and bounding a geometrical reference surface defined as the shape which the cornea has when the support is applied thereto via its base portion, an inner tubular member disposed coaxially with the inside of the support and withdrawn towards the inside of the support in relation to the reference surface, means for guiding the body in rotation around the axis of the support in relation to the support, through at least 360°, means for entraining the body in rotation around the axis of the support in relation to the support through at least 360°, a blade disposed inside the body, having an own direction and having in a predetermined sense of its own direction a cutting tip, means for connection between the blade and the body which comprise means for displacing the blade in a controlled manner in translation along its own direction in relation to the body, between an inoperative position, in which the blade is withdrawn towards the inside of the body in relation to the reference surface and in which the tip is turned towards said reference surface, and a cutting position in which the tip projects outside the body in relation to the reference surface in a manner offset with respect to the axis of the support, characterized in that the means of connection between the blade and the body also comprise means for displacing in a controlled manner the blade in the orientation of its own direction in relation to the body, between a number of predetermined orientations, including a first orientation in which its own direction is parallel with the axis of the support, and a second orientation in which its own direction intersects the axis of the support and is so inclined in relation to the axis that, at least in the cutting position, the tip of the blade diverges in said direction in relation to the axis, while maintaining in said orientations a substantially identical distance between the axis of the support and a zone in which the tip of the blade crosses the reference surface in the cutting position.

Although a, for example, continuous adjustment of the orientation of the blade between a large number of orientations does not exceed the scope of the present invention, said predetermined orientations are preferably two in number in relation to said first and second orientations; this enables the keratotome according to the invention to be made in a particularly simple i.e., both economical and reliable manner, as will be explained hereinafter.

Preferably, the keratotome according to the invention comprises inside the base portion a wall rigidly connected to the body and having towards the outside of the body a face coinciding with the reference surface, said wall having means for the passage of the blade into the cutting position. When the blade penetrates into the cornea of the receiving eyeball, said wall prevents the deformation of the cornea, in relation to which the keratotome is preferably also retained by the fact that the base portion bounds an annular cavity open around the reference surface, and by the fact that means are provided for putting the annular cavity under negative pressure; as a result, relative displacement between the keratotome and the cornea to be incised is obtriated, and the cornea can be cut into in accordance with a fully predetermined geometry, thereby ensuring closure of the incision on itself when the body and the blade rotate jointly in the cutting position in relation to the support, and subsequent satisfactory correspondence between the optical axis of the optical zone of the lense and the visual axis of the receiving eyeball, since the keratotome has itself been placed coaxially in relation to the visual axis prior to the incision. To this end, said wall preferably comprises means for seeing through the wall and/or for defining the positioning in relation to the cornea of the receiving eyeball.

BRIEF DESCRIPTION OF THE DRAWINGS

Other features and advantages of the lense for keratometry and the keratotome according to the invention, as well as an operational technique for putting the lense according to the invention into place, more particularly by making an incision using the keratotome according to the invention, will appear from the succeeding description of several exemplary embodiments of the invention, as illustrated in the accompanying drawings.

FIG. 1 is a plan view of a lense according to the invention, showing the front faces of its optical zone, and anchoring zone respectively.

FIG. 2 illustrates the placemat of such a lense on the cornea of a receiving eyeball, sectioned along a plane II—II including the optical axis of the lense optical zone and the visual axis of the receiving eyeball. The left-hand half of FIG. 2 illustrates the incision made for this purpose in the cornea of the receiving eyeball and the lense prior to insertion of the cornea anchoring zone in the incision, while the right-hand half of FIG. 2 shows the lense and cornea after insertion of the lense anchoring zone in the incision in the cornea.

FIG. 3 shows, in greatly enlarged scale, a detail of the lense portion indicated at III in FIG. 2.

FIG. 4 shows, in a view similar to that of FIG. 3, a different embodiment of the lense illustrated in FIGS. 2 and 3.

FIG. 5 illustrates, in a view similar to that of FIG. 2, the positioning of a lense according to the invention which differs from that illustrated in FIG. 2.

FIG. 6 shows, in a view similar to that of FIG. 3, a detail referenced as VI in FIG. 5.

FIG. 7 shows, in a view similar to that of FIG. 4, a different embodiment of the lense illustrated in FIGS. 5 and 6.

FIG. 8 shows a keratotome according to the invention, sectioned through a plane VIII—VIII in FIG. 9 and including the axis of relative rotation of the inner body and the outer support, said axis coinciding with the visual axis when the keratotome is in use.

FIG. 9 shows a detail of the keratotome, viewed as indicated by arrow IX in FIG. 8, parallel with the axis of relative rotation of the inner body and outer support.

FIG. 10 shows another detail of the keratotome, sectioned along a plane X—X in FIG. 8, said plane being perpendicular to the plane VIII—VIII in FIG. 9 and inclined with respect to the axis of relative rotation of the inner body and the outer support.

FIG. 11 is a sectional view along a plane XI—XI in FIG. 10, said plane coinciding with the plane VIII—VIII in FIG. 9.

FIG. 12 shows the blade of the keratotome according to the invention in elevation in the direction indicated by arrow XII in FIG. 11.

DETAILED DESCRIPTION

Reference will be made in the first place to FIGS. 1 to 3, showing a lense 1 for keratometry made according to the invention, preferably by the molding followed by processing, more particularly laser processing of at least one flexible and biocompatible polymer selected from natural and synthetic polymers such as, for example, collagen or a collagen copolymer. Naturally, the lense 1 must be transparent and maintain its transparency over time and in contact with cornea 2 (FIG. 2) of a receiving eyeball.

In known manner, the lense 1 comprises two zones, namely an optical zone 3 and an anchoring zone 4.

The optical zone 3 has, also in known manner, the shape of a lense having an optical axis 5 coinciding with the visual axis of the receiving eyeball when the lense is put in place thereon. The optical zone 3 is bounded by a convex front face 6 and a concave rear face 7 respectively which, when the lense is put in place on the cornea of the receiving eyeball, are turned towards the outside of the eyeball and towards its cornea 2, respectively, the rear face 7 of the lense 1 conforming to a surface zone 18 of the cornea. The faces 6 and 7 have respective geometries, determined in a manner familiar to those skilled in the art, both relative to applying the rear face 7 tightly against the surface 18 of the cornea 2 of the receiving eyeball, and relative to predetermined optical characteristics corresponding to the correction which is to be given to the receiving eyeball. In the case of an anastigmatic receiving eyeball, the two faces 6 and 7 have the shape of spherical caps each centered on the optical axis 5, and precisely such a case is illustrated in FIGS. 1 to 3, in which the optical zone 3 takes the form of a divergent lense adapted to correct myopia, although it should be understood that it will not exceed the scope of the invention to give the optical zone 3 the shape of a convergent lense to correct hypermetropy. In the case of an astigmatic receiving eyeball, one of the two faces of the optical zone 3, preferably its rear face 7, can also be non-spherical, while its other face, i.e., its front face 6, can remain spherical and centered on the axis 5, but in such a case it is preferred to shape the lense according to the invention in the manner to be described with reference to FIGS. 5 to 7.

Preferably, the minimum thickness of the optical zone 3 is at least about 0.2 mm, although a smaller minimum thickness might be adopted, for example, of the order of approximately 50 $\mu$m, said thickness being measured along the axis 5 in the case of a divergent optical zone 3 or along the periphery of the optical zone 3 in the case of a convergent optical zone 3, this number being indicated merely by way of non-limiting example.

In the direction away from the axis 5, the two faces 6 and 7 of the optical zone 3 are bounded by respective peripheries 8, which, in the case of spherical faces 6 and 7 centered on the axis 5, are circular and disposed in respective planes (not shown) perpendicular to the axis 5 and which, in the case of a non-spherical face 6 or 7, have a somewhat non-circular shape determined by the intersection of such face 6 or 7, respectively, with a corresponding face 10, 11, respectively, to be described hereinafter, of the anchoring zone 4. Naturally, the respective diameters of the circular or substantially circular peripheries (in which case a mean diameter is considered) 8 and 9 are so determined that the optical zone 3 covers the whole of the visual field of the receiving eyeball; for a receiving eyeball of a human adult, the periphery 8 of the front face 6 has a diameter $D_1$ of about the order of 5 to 7 mm, these numbers being indicated by way of non-limiting example, while the periphery 9 of the rear face 7 has a diameter $D_2$ smaller by at most a few tenths of a millimeter $D_1$ determined in dependence on the value of $D_1$ by dimensional characteristics of the anchoring zone 4, which will now be described.

The anchoring zone 4, which is a feature of the lense according to the invention, has a generally annular shape of revolution around the optical axis 5 and edges the optical zone 3 in the direction away from the optical axis 5.

According to the invention, the anchoring zone projects in relation to the rear face 7 of the optical zone 3, and is also offset rearwardly in relation to the front face 6 thereof. In the embodiment illustrated in FIGS. 1 to 3, therefore, it is bounded by a front face 10 and a rear face 11 which are both truncated faces of revolution around the axis 5 towards which they are connected respectively to the front face 6 of the optical zone 3, directly along the generally circular periphery 8 thereof, and to the rear face 7 of the optical zone 3, directly along the circular or substantially circular periphery 9 thereof. The periphery 8, 9 of the front face 6 or rear face 7, respectively, of the optical zone 3 thus has the shape of a respectively projecting or re-entrant edge. In a variant illustrated by a chain-dot line in FIG. 3, concerning the connection of the front face 10 of the anchoring zone 4 to the front face 6 of the optical zone, said edge can be replaced by a transitional zone 8' of respectively convex or concave rounded shape which connects without abrupt transition with the corresponding faces of the optical zone 3 and the anchoring zone 4. From their connection with the front face 6 and rear face 7 of the optical zone 3, respectively, the two faces 10 and 11 of the anchoring zone 4 converge in the direction away from the optical axis 5 and are connected to one another along a peripheral edge 12 of the lense, said peripheral edge 12 having in the embodiment illustrated in FIGS. 1 to 3 the shape of a circular edge centered on the axis 5 and lying in a plane (not shown) perpendicular to axis 5. Having regard to the possible fragility of such an edge 12, a variant embodiment of the lense 1 illustrated in FIGS. 1 to 3 can also be adopted in which, as illustrated in FIG. 4, the front face 10 and the rear face 11 of the anchoring zone 4 are connected to one another not directly, but via a, for example, cylindrical peripheral face 13 of revolution around the axis 5; parallel with the axis 5, the face 13 has however as limited a dimension $e_1$ as possible, for example, of the order of 50 $\mu$m at most, this number being given by way of non-limiting example; with reference to the axis 5, the edge 12 or the face 13 substituted therefor has a diameter $D_3$ greater than $D_1$, for example, of the order of 7 mm to 9 mm for the values of $D_1$ indicated hereinbefore, these numbers being given merely by way of non-limiting example.

In a manner characteristic of the present invention, the front face 10 and rear face 11 of the anchoring zone 4, when viewed in section along a half-plane bounded by the optical axis 5, as is the case in FIGS. 2 and 3 or, in a different embodiment, in FIG. 4, have a shape and dimensions which are at least substantially identical, i.e., in the embodiment illustrated, the shape of segments of straight lines of the same length 1, the value of 1 being advantageously of the order of approximately 0.5 mm to 1.5 mm. These values are given merely as non-limiting examples and correspond on the one hand to the values $D_1$ and $D_3$ indicated hereinbefore, and on the other hand to respective inclinations A and B of the rear face 11 and the front face 10, in relation to a plane 350 perpendicular to the axis 5, of between approximately 40° and 45° and between approximately 50° and 55°, these numbers also being given merely by way of non-limiting example. In fact, for A a value of 42° is preferred, adopting for B a value which derives therefrom, having regard to the other dimensional characteristics of the lense 1, the value of B being of course greater than the value of A, while remaining substantially below 90°, although other values can be adopted without exceeding the scope of the present invention. Similarly, the scope of the present invention would not be exceeded if shapes other than a truncated shape of revolution around the optical axis 5 were adopted for the faces 10 and 11, on condition that the mutual convergence of said faces in the direction away from the axis 5 is preserved, with direct connection (FIGS. 2 and 3) or substantially direct connection (FIG. 4) of said faces in the direction away from the optical axis 5, and maintaining at least substantially identical shapes and dimensions of said faces 10 and 11, when they are viewed in section along a half-plane bounded by the optical axis 5. In such a case, the dimensions 1 must be considered as the length of the rectilinear development of the sections of the faces 10 and 11 thus conceived by a half-plane including the axis 5, and A and B are mean inclinations of the faces 10 and 11 in relation to a plane perpendicular to the axis 5. When the truncated respective front face 10 or rear face 11 of the anchoring zone 4 is connected to the front face 6 or rear face 7, respectively of the optical zone 3 via a rounded transitional zone such as 8', the development of said transitional zone 8', when it is viewed in section along a half-plane bounded by the optical axis 5, enters by about one half into the calculation of the value 1, of which this development may represent up to one half, and by approximately one half into the calculation of $D_1$ in respect of which this development is in fact substantially negligible.

Under these conditions, the lense 1 described with reference to FIGS. 1 to 3, or its variant described with reference to FIG. 4, can be put into place on the cornea 2 of a receiving eyeball by a process which will now be described with reference to FIG. 2.

In a first phase of this process, after the epithelium has been withdrawn, for example, by means of alcohol (90°) in the surface zone 18 of the cornea 2 intended to receive the lense 1, there is made in the cornea 2 an incision 14, illustrated in the left-hand portion of FIG. 2, having a shape and dimensions corresponding to those of the rear face 11 of the anchoring zone 4 of the lense 1. In other words, referring specifically to the examples described, in which the rear face 11 has a truncated shape of revolution around the axis 5, between a circle of diameter $D_2$ (periphery 9 of the rear face 7 of the optical zone 3) and a circle of diameter $D_3$ (the diameter of the peripheral edge 12 or the peripheral face 13), with an inclination A in relation to a plane perpendicular to the optical axis 5, an incision 14 is made which is a truncated incision of revolution around the visual axis of the eyeball 2 (said axis coinciding with the optical axis 5 in FIG. 2), with an inclination equal to A in relation to a plane 15 perpendicular to the visual axis, such incision 14 having at its emergence from the cornea 2 the shape of a circle 16 centered on the axis 5 and lying in a plane (no reference) perpendicular to the axis 5, with a diameter equal to $D_2$, while it terminates inside the cornea 2 in a circular bottom edge 17 also centered on the axis 5 and lying in a plane (the plane 15 in the example illustrated) perpendicular to the axis 5, with a diameter $D_9$ at least equal to $D_3$, and preferably greater than $D_3$, for example, at least approximately 0.5 mm. It will be noted that, having regard to the preferred dimensions indicated hereinbefore and in the case of an eyeball of a human adult, the incision 14 thus made, although it opens into the surface 18 of the cornea 2 in a still central zone thereof, of comparatively reduced thickness, enters the cornea 2 at an inclination in relation to the cornea surface 18 in the direction of peripheral zones of comparatively larger thickness, so that it only slightly weakens the cornea 2 mechanically.

The incision 14 is therefore made continuously all around the cornea 2, for example, by means of the keratotome which will be described hereinafter with reference to FIGS. 8 to 12, and thus has two flanks 19, 20 which are both truncated flanks of revolution around the axis 5 and initially identical.

After the incision 14 has thus been made, the lense 1 is positioned facing the cornea 2 and, by relative movements produced by pushing the lense by means of a pad, the anchoring zone 4 is inserted inside the incision 14 between its flanks 19 and 20 To facilitate insertion, the anchoring zone 4 is preferably provided, for example, in diametrically opposite positions with respect to the optical axis 5 of the optical zone 3, with notches 21 opening into the peripheral edge 12 (or into the peripheral face 13, as the case may be) and also into the front face 10 and rear face 11 of the anchoring zone 4, it being understood that such notches 21 may be omitted, or provided in a number other than two. However, it will be noted that in the case of a lense intended to correct astigmatism, two notches diametrically opposite in relation to the optical axis 5, as illustrated, form a convenient means for locating the angular positioning of the lense around the optical axis 5, it being understood that other means could be substituted for this purpose.

During insertion, the anchoring zone 4 moves the two flanks 19 and 20 of the incision 14 progressively away from one another and, on completion of the insertion, while the optical axis 5 of the optical zone 3 coincides with the visual axis of the eye and the rear face 7 of the optical zone 3 fits onto the zone of the surface 18 of the cornea 2 situated outside the circle 16, the rear face 11 of the anchoring zone 4 fits onto the flank 19 of the incision 14, without deformation of the cornea at that location. The peripheral edge 12 (or the peripheral face 13, comparable with good approximation to such an edge) practically fits onto the circle 17 interconnecting the two flanks 19 and 20 of the incision 14, while the flank 20 of the incision 14 fits onto the rear face 10 of the anchoring zone 4. This slightly deforms outwards a strip 22 of the cornea 2 situated between the flank 20 of the incision 14 and the surface 18 of the cornea 2, as shown in the right-hand portion of FIG. 2. Studies have shown that the deformation thus undergone by the cornea 2 was strictly limited to zones close to the circle 17, and was perfectly tolerable; more particularly in the direction of the axis 5 the strip 22 terminates in a circular edge 23, resulting from the spreading of the strip 22 at the level of the circle 16 at the generally circular periphery 8 of the front face 6 of the optical zone 3, to which the strip 22 is thus connected without forming any excess thickness which might subsequently cause trouble by contact with the eyelids, and substantially without any break which might be subsequently filled with collagen generated by the cornea 2 with the formation of a whitish ring, or might cause the subsequent formation of a troublesome fillet of epithelium.

After the anchoring zone 4 of the lense 1 has thus been inserted in the incision 14, this location is sutured in the usual manner and with the usual precautions, whereafter a dressing is put in place which is retained for the time necessary for the epithelisation of the front face 6 of the lense 1, in practice a few days. It is also possible to dispense with any suture, having regard to an interfitting effect resulting from the satisfactory mutual adaptation of the respective shapes of the anchoring zone 4 of the lense and the corresponding zones of the cornea 2, i.e., more particularly the strip 22 thereof.

For reasons of convenience of incision, whatever the shape of the front and rear faces of the optical zone of the lense according to the invention may be, and for reasons of facility in the production design of the lense when at least one of said faces is non-spherical, however, it is preferred to use a lense according to the invention of a kind illustrated in FIGS. 5 and 6 or, as a variant, in FIG. 7.

The lense 101 according to the invention (FIGS. 5 and 6, or the variant illustrated in FIG. 7), is very similar to the lense illustrated in FIGS. 1 to 3 (or the variant illustrated in FIG. 4), so that in FIGS. 5 and 6 the references 6 to 12 and in FIG. 7 the reference 13 are used to denote portions of the lense 101 or its variant identical with the portions described with like references in connection with the lense 1 or its variant illustrated in FIG. 4. More particularly, the geometrical arrangements characteristic of the invention, and also the dimensional characteristics shown by way of non-limiting example in relation to the embodiment illustrated in FIGS. 1 to 3 and the variant illustrated in FIG. 4, can be repeated in connection with the lense 101 illustrated in FIGS. 5 and 6 and its variant illustrated in FIG. 7.

The lense 101 illustrated in FIGS. 5 and 6 and its variant illustrated in FIG. 7 differ from the lense 1 illustrated in FIGS. 1 to 3 and its variant illustrated in FIG. 4, respectively, only by the method of connection of the front face 10 and rear face 11 of the anchoring zone 4 to the front face 6 and rear face 7 respectively, of the optical zone 3.

In the case of the lense 101 illustrated in FIGS. 5 and 6 and its variant illustrated in FIG. 7, the front face 10 of the anchoring zone 4 is connected to the periphery 8 of the front face 6 of the optical zone 3 via an annular, for example, a cylindrical face 102 of revolution around the optical axis 5, said face 102 being turned in the direction away from the axis 5, so as to form a discontinuity in relation to the front face 6 of the optical zone 3, parallel with the axis 5. The face 102 has a dimension $e_2$ which is small in relation to the other dimensions of the lense 101, i.e., of the same order of magnitude as the dimension $e_1$ described with reference to FIG. 4 shown in FIG. 7, namely, a value of the order of approximately 50 μμm at most, such value being given merely by way of non-limiting example. The rear face 11 of the anchoring zone 4 is connected to the periphery 9 of the rear face 7 of the optical zone 3 via a, for example, cylindrical face 103 of revolution around the axis 5, to which said face 103 is however turned so as to form a projection in relation to the rear face 7 of the optical zone 3; parallel with the axis 5, the face 103 has substantially the same dimension $e_2$ as the face 102. When the front face 6 and rear face 7 of the optical zone 3 are spherical, their peripheries 8, 9 are circular, but when at least one of them is non-spherical, its periphery 8, 9 has a shape differing from a circular shape, although close thereto, but it is situated on a cylinder of revolution around the axis 5 when the face 102 or the face 103 is itself respectively a cylindrical face of revolution around the axis 5; of course, the faces 102 and 103 have the same diameters $D_1$, $D_2$ as the peripheries 8 and 9 of the front face 6 and rear face 7 of the optical zone 3, respectively, when said faces 102 and 103 are both cylindrical faces of revolution around the axis 5, as is preferred. In the case of an other than cylindrical shape, while still being a shape of revolution around the axis 5, each of the faces 102 and 103 progressively widens from its connection to the periphery 8, 9 of the front face 6 or rear face 7 of the optical zone 3, respectively, until it is connected to the front face 10 of the anchoring zone 4 or its rear face 11, respectively.

It will be noted that a cylindrical shape of revolution of the two faces 102 and 103 allows the connection, in a geometrically very simple manner, of an anchoring zone 4 having a strict shape of revolution around the axis 5, more particularly via its front face 10 and rear face 11, to an optical zone 3 having a shape other than a strict shape of revolution around the axis 5, as is the case when at least one of said faces 6 and 7 is non-spherical. In this respect, the lense 101 illustrated in FIGS. 5 and 6 and its variant illustrated in FIG. 7 are more suitable than the lense illustrated in FIGS. 1 to 3 or its variant illustrated in FIG. 4 for the correction of astigmatism. It will also be noted that in such a case the notches 21 which can advantageously be provided also on the lense 101 illustrated in FIGS. 5 or 6 or its variant illustrated in FIG. 7 can serve to locate the axis of astigmatism and to suitably orientate the lense during its positioning on the cornea. Naturally, the face 102 or 103 ensuring the connection between the anchoring zone 4 and the non-spherical face 6 or 7 of the optical zone 3 has a dimension $e_2$ which varies between a maximum and a minimum but, to the extent possible, values are retained which are as similar as possible for the dimensions of the faces 102 and 103, respectively, parallel with the axis 5.

Whatever the shapes adopted for the faces 102 and 103 may be, said shapes are so coordinated that, in a view sectioned along a half-plane including the axis 5, the faces 102 and 103 occupy positions as close as possible in relation to the front face 10 of the anchoring zone 4 and its rear face 11, respectively.

Under these conditions, the positioning of the lense 101 illustrated in FIGS. 5 and 6 or its variant illustrated in FIG. 7 is performed in the manner illustrated in FIG. 5, i.e., by first making in the cornea 2, via its face 18 and after the localized withdrawal of the epithelium, an incision 114 produced, just like incision 14, without the removal of material, and having a shape corresponding to that of the assembly of the rear face 11 of the anchoring zone 4 and the face 103 ensuring its connection to the periphery 9 of the rear face 7 of the optical zone 3 of the lense, as can be gathered from an examination of the left-hand portion of FIG. 5.

More precisely, incision 114 opens on to the face 18 of the cornea 2 via a circle 16 identical with that described with reference to FIG. 2, i.e., having the diameter $D_2$ of the circular or substantially circular periphery 9 of the rear face 7 of the optical zone 3 towards the inside of the cornea 2 starting from the circle 16, and when viewed in section along a half-plane bounded by the axis 5, the incision 14 reproduces the shape of the face 103 and of the rear face 11 of the anchoring zone 4. In other words, when the face 103 has a cylindrical shape of revolution around the axis 5, as is preferred, the incision 114 has, directly adjacent the circle 16 via which it opens onto the face 18 of the cornea 2, a cylindrical zone 115 of revolution around the axis 5 having a diameter equal to $D_2$ and bounded respectively in the direction of the axis 5 and the direction away from the axis 5 by flanks 120 and 121 which are both cylindrical flanks of revolution around the axis 5 with, parallel thereto, a dimension equal to the dimension $e_2$ or to a mean value of the dimension $e_2$ when the rear face 7 of the optical zone 3 of the lense non-spherical. Towards the inside of the cornea 2, said zone 115 is connected via a circular edge 115, identical with the circle 16, to a zone 117 identically reproducing the incision 14 described with reference to FIG. 2, i.e., bounded by two flanks 19 and 20 which are truncated flanks of revolution around the axis 5 and reproducing the rear face 11 of the anchoring zone 4, identically except that they are prolonged further than the latter from the axis 5, said flanks 19 and 20 being connected to one another via a circular end edge 17 in the direction away from the optical axis 5. The insertion of the lense 101 illustrated in FIGS. 5 and 6 or its variant illustrated in FIG. 7 into the incision 114 is performed as disclosed hereinbefore in connection with the lense 1 illustrated in FIGS. 1 to 3 or its variant illustrated in FIG. 4 and the incision 14. Prior to insertion, the incision 114 is in the closed state, as illustrated in the left-hand portion of FIG. 5, and the anchoring zone 4 is progressively inserted thereinto by relative movements of the lense and the cornea 2, first moving the flanks 120 and 121, and then the flanks 19 and 20, away from one another until the lense 101, or its variant illustrated in FIG. 7, arrives in the position illustrated in the right-hand portion of FIG. 5, in which the rear face 7 of the optical zone 3, the face 103, the rear face 11 of the anchoring zone 4, the peripheral edge 12 or peripheral face 13, the front face 10 of the anchoring zone 4 and the face 102 respectively fit onto the zone of the surface 18 of the cornea 2 situated inside the circle 16, the flank 120 of the zone 115 of the incision 14, the flank 19 of the zone 117 thereof, the end edge 17 with a slight clearance, the flank 20 of the zone 117 of the incision 114, and the flank 121 of the zone 115 thereof, moving away a strip 118 of cornea 2 situated between the incision 114 and the cornea surface 18. For readily understandable geometrical reasons, the strip 118 is connected via a circular edge 119, corresponding to the connection of the flank 117 of the zone 115 of the incision 114 with the surface 18 of the cornea 2 at the level of the circle 16 during the making of the incision 14, to the periphery 8 of the front face 6 of the lense substantially without a break, i.e., with the advantages already described with reference to FIG. 2.

The anchoring zone 4 is then sutured with the cornea 2 in known manner, taking the usual precautions, whereafter a dressing is put in place for the time required for the epithelisation of the front face 6 of the lense 1. However, suturing of the anchoring zone 4 on the cornea 2 is not indispensible, the anchoring zone 4 being retained under the corner strip 22 by an interfitting effect.

Of course, the embodiments of a lense according to the invention which have just been disclosed are merely non-limiting examples which may be modified in numerous ways without exceeding the scope of the present invention. More particularly, variations might relate to the method of connecting the front and rear faces of the anchoring zone with the front and rear faces of the optical zone, respectively, one of such connections possibly being direct, as disclosed with reference to FIGS. 1 to 4, and the other indirect, as disclosed with reference to FIGS. 5 to 7.

Whatever the embodiment adopted for the lense according to the invention may be, the form of incision to be made to receive the lense in the cornea 2 can be readily determined by those skilled in the art.

The incision can be performed manually, which requires great skill. However, no prior art keratotomes or corneal trepans enable it to be performed.

The present invention therefore provides a keratotome for making such an incision. A non-limiting exemplary embodiment of such a keratotome will now be described with reference to FIGS. 8 to 12, in the first place to FIG. 8, in which the keratotome is denoted by the reference 200.

To enable it to be gripped by the surgeon and positioned on the surface 18 of the cornea 2 to be incised, the keratotome 200 comprises an outer support 201 having the general shape of a tubular wall of revolution around an axis 202 and enclosing an inner body 203 also having the form of a tubular wall of revolution around the axis 202, with the possibility of relative rotation around said axis 202 to the exclusion of any other possible relative displacement.

More precisely, the outer support 201 has a general truncated shape of revolution around the axis 202 and diverges from an annular base portion 204 of revolution around the axis 202 and adapted to be applied to the surface 18 of the cornea 2 to be incised, around the location of the incision 14 or 114 to be made, as far as an annular head portion 205 of revolution around the axis 202 and adapted for the gripping of the outer support 201 by the surgeon's other hand.

To allow relative immobilization of the outer support 201 and the cornea 2 to be incised, the wall forming the outer support 201 is doubled in zone adjacent the base portion 204, so as to define immediately adjacent said base portion 204 an annular cavity 206 of revolution around the axis 201 and opening into the base portion 204 via an annular slot 207 of revolution around the axis 202. The slot 207 is bounded, respectively in the direction towards and away from the axis 202, by two annular bearing surfaces 208, 209 of revolution around the axis 202 and situated on the same reference surface 210 reproducing the shape of the surface 18 of the cornea 2 supposed in a relation of coincidence between the visual axis and the axis 202. Naturally, having regard to possible differences in shape between the surfaces 18 of different corneas 2, the reference surface 210 is so selected as to correspond to the majority of cases and in such a way that the surfaces 18 of corneas 2 having slightly different shapes can adapt themselves thereto by a suctional effect in the direction of the inside of the cavity 206 via the slot 207, resulting from the connection of said cavity 206 to means 211 enabling a relative negative pressure to be established therein, said means 211 being separate from the keratotome 200 and connected to the cavity 206 via a connecting end 213 thereof placed projecting on the outer support 201, in the direction away from the axis 202, between the base portion 204 and the head portion 205, and via a flexible conduit 212. By way of non-limiting example, the bearing surfaces 208 and 209 can be bounded, in the direction towards and away from the axis 202 respectively, by a circle (no reference) of diameter $D_4$ greater than $D_2$ and preferably than $D_3$ and, for example, of the order of 11.4 mm, and by a circle (no reference) of diameter $D_5$ greater than $D_4$, and, for example, of the order of 15.5 mm.

By its head portion 205 the outer support 201 bounds an annular groove 214 of revolution around the axis 202 and open in the direction thereof. More precisely, the groove 214 is bounded in the direction away from the axis 202 by a cylindrical end face 215 of revolution around the axis 202 and having as large a diameter as possible, having regard to the dimensions of the head portion 205. In the direction of the base portion 204 and opposite therefrom respectively, the groove 214 is bounded by flat annular faces 216, 217 of revolution around the axis 202, to which said faces 216 and 217 are perpendicular; said faces 216 and 217 connect the end face 215 of the groove 214 to respective faces 218, 219 of the outer support 201, which are cylindrical faces of revolution around the axis 202, towards which they are turned; the face 218 connects the face 216 to a truncated face 220, of revolution around the axis 202, of the support 201 and connects as it converges the face 218 to the bearing surface 208 of the base portion 204 of the support 201. The face 219 connects the face 217 to an annular flat face 221 of revolution around the axis 201, said face 221 being turned oppositely from the base portion 204 and bounding the outer support 201 oppositely from the base portion 204. The support 201 just described is advantageously formed by a number of members assembled together by a means enabling them to be disassembled as required, for example, by screwing, so that the support 201 can readily be cleaned and if necessary have its base portion 204 interchanged for a base portion whose bearing surfaces 208 and 209 are differently shaped, for example, to allow the use of the same keratotome 200 on eyeballs having very different geometrical conformations.

The outer support 201 cooperates via the groove 214 and the face 218 with the inner body 203 to ensure the guidance of the latter in rotation around the axis 202, without any other possible relative movement.

To this end the body 203 is bounded in the direction away from the axis 202 more particularly by a cylindrical face 222 of revolution around the axis 202 with a diameter substantially identical to that of the face 218, with which said face 222 is placed in intimate contact but with the possibility of sliding, so that the mutual contact ensures the guiding of the body 203 in rotation around the axis 202, and by an also cylindrical face 223 of revolution around the axis 202 and having a diameter slightly smaller than that of the face 219 opposite which it is placed, without mutual contact. Between the faces 218 and 219 the body 203 has projecting outwardly in relation to the axis 202 two shoulders 224, 225 of a general annular shape of revolution around the axis 202 and engaging in the groove 214 adjacent the face 216 thereof and the face 217 thereof respectively, but without contact with any of the faces 215 to 217 of the groove 214. However, the shoulder 224 nearest to the face 216 of the groove 214 has in the direction of said face 216 a flat annular face 226 of revolution around the axis 202, to which it is perpendicular, and the inner body 203 bears against the outer support 201, in a direction of the axis 202 extending from the face 226 in the direction of the face 216, via the contact of the face 226 with a set of balls 227 themselves partially engaging in a groove 228 with which the face 216 is formed and which has an annular shape of revolution around the axis 202. Advantageously the balls 227 are retained in a relation of constant mutual angular separation with reference to the axis 202 by a cage 229 made of a material having a low coefficient of friction and interposed between the faces 226 and 216. The shoulder 225 closest to the face 217 has in the direction thereof a flat annular face 230 of revolution around the axis 20 and perpendicular thereto, and interposed between the faces 217 and 230 are annular washers 231 of revolution around the axis 202 which are made from a material having a low coefficient of friction and enable the two shoulders 224 and 225 to be retained without clearance, parallel with the axis 202, between the faces 216 and 217 of the outer support 201.

The body 203 can therefore rotate around the axis 202 inside the support 201 through at least 360° and preferably without limitation. Of course, other means might be selected to ensure the guiding of the body 203 and the support 201 in relative rotation around the axis 202, just as the body 203 and the support 201 might take shapes different from those described and illustrated.

To enable the surgeon to produce such a rotation through at least 360° at will, entraining means 232 are provided of known design, for example, the design disclosed in granted European Patent No. 0 047 190, it being understood that other means might also be provided to this end.

To cooperate with the said entraining means 232, the shoulder 224 takes in the direction away from the axis 202, inside the groove 214, the form of a toothed ring 233 which meshes with a pinion 234 mounted to rotate in relation to the outer support 201 around an axis 235 parallel with the axis 202 and offset in relation to the groove 214 in the direction away from the axis 202. To this end, the end face 215 is formed between the axes 202 and 235 with a notch (no reference) through which the pinion 234 passes, and the head portion 205 of the support 201 bears in a rigidly connected manner, projecting in the direction away from the axis 202 opposite said notch, a double seat 236 which defines a first bearing 237 disposed between the pinion 234 and the face 221 of the support 201 and receives for relative rotation around the axis 235, without any other possibility of relative displacement, a shaft 238 rigidly connected to the pinion 234. Opposite the pinion 234 in relation to the bearing 237 the shaft 238 bears rigidly connected, a bevel gear 239 meshing with another bevel gear 240 disposed opposite the axis 202 in relation to the axis 235 and having an axis 241 inclined in relation to the axis 235; to ensure the guidance of the gear 240 in rotation around its axis 241, via a shaft 242 rigidly borne coaxially by the pinion 240, the double seat 236 defines a second bearing 243 of axis 241, through which the shaft 242 entirely extends to present, opposite the bearing 243 in relation to the bevel gear 240, a manually operable button 244 or means for connection to an electric or pneumatic driving motor (not shown).

In a manner which is not shown but which can easily be envisaged by a man skilled in the art, indexing means are provided to at least locate the angular position of the inside body 203 around the axis 202 in relation to the outer support 201, for example, in the form of graduations borne by the face 221 of the support 201 and by a flat annular face 245 of revolution around the axis 202 to which the face 223 of the body 203 is connected opposite its connection to the shoulder 225 and which is located coplanar with the face 221, in the same orientation as the latter. However, means are preferably also provided to immobilise as required the body 203 in rotation around the axis 202 in relation to the support 201 in a predetermined position, for example, by the provisional locking of the manual drive button 244, as described in the aforementioned granted European patent.

Opposite its connection to the shoulder 224, the face 222 of the body 203 is connected to a face 246 thereof which has a truncated shape of revolution around the axis 202, is turned in the direction away from the axis 202, and is situated opposite the face 220 of the outer support 201, parallel therewith and having regard to a continuous relative clearance 247, so as to avoid any contact between the faces 246 and 220 and therefore any impediment to the relative rotation of the body 203 and the support 201.

The face 246 thus extends from its connection to the face 222 a far as its connection to a flat annular end face 248 of revolution around the axis 202, to which said face 248 is perpendicular, said face 248 forming the extreme limit of the body 203 in the direction of the base portion 204 of the support 201. Like the whole of the body 203, said end face 248 is disposed withdrawn towards the inside of the support 201 in relation to the reference surface 210 defined hereinbefore.

In the direction of the axis 202 the face 248 of the body 203 connects the face 246 thereof to a cylindrical face 249 of revolution around the axis 201, towards which said face 249 is turned. The face 249 connects the face 248 to a face 250, which is a truncated face of revolution around the axis 202, towards which it is turned, said face 250 diverging from its connection with the face 249 to its connection with a truncated face 251 of revolution around the axis 202, towards which said face 251 is turned, said face 251 having an inclination which is smaller than the inclination of the face 250 in relation to the axis 201 and is in practice identical to that of the face 246, so that the faces 251 and 246 are parallel with one another. The face 251 itself connects the face 250 to a cylindrical face 252 of revolution around the axis 202, towards which the face 252 is turned. The face 252, parallel with the face 218, thus connects the face 251 to the face 245 of the body 203. The body 203 therefore bounds an internal cavity 257 around the axis 202.

Like the support 201, the body 203 is advantageously produced by assembling a number of members together, with the possibility of disassembly with a view to maintenance operations or a change in the dimensional characteristics more particularly due to a wish to use the same keratotome 200 on eyeballs having very different dimensions.

The fact is that, like the support 201 in its base portion 204, the body 203 is adapted to tightly fit the surface 18 of the cornea 2 to be incised, by a wall 253 having the general shape of a cap of revolution around the axis 202, said wall 253 closing the body 203 in the direction of the base portion 204 of the support 201 inside the face 249 and having to this end towards the base portion 204 a face 254 which tightly fits the reference surface 210—i.e., in the form of a concave spherical cap centered on the axis 202. Via said face 254 the wall 253 contacts the surface 18 of the cornea 2, but without applying any pressure thereto. By way of non-limiting example, the wall 253 is retained rigidly but detachably by peripheral engagement in an annular groove 255 of revolution around the axis 202, with which the face 249 is formed adjacent the face 248 and which is turned towards the axis 202, said groove 255 being bounded by two screwed-together members (no references) of the body 203, to enable the wall 253 to be changed.

Opposite its face 254, the wall 253 has a convex face 256 which is parallel with the face 254 and thus bounds the internal cavity 257 of the body 203 in the direction of the base portion 204; the cavity 257 opens opposite the base portion 204 of the support 201 via an orifice 258 bounded by the face 245 in the direction away from the axis 202 and enabling the wall 253 to be seen through the cavity 257. To facilitate the positioning of the keratotome 200 with an exact correspondence between its axis 201 and the visual axis on the cornea 2 to be incised, the wall 253 is advantageously continuously formed along the axis 202 with a cylindrical hole 250 of revolution around the axis 201 having as small a diameter (no reference) as possible, for example, of the order of 0.05 mm; it is moreover preferably widely opened up to enable the surgeon to see the surface 18 of the cornea 2 during the incision through the orifice 258 and the cavity 257; this is illustrated, for example, in FIG. 9 by seven large orifices 260, it being understood that this example is non-limiting and that more particularly the orifices 260 might be replaced with a larger number of smaller orifices, giving the wall 253 the appearance of a grid; since during the use of the keratotome 200—i.e., the rotation of the body 203 in relation to the support 201 fixed in relation to the cornea 2—the face 254 of the wall 253 moves in contact with the surface 18 of the cornea, the orifices 260, or the orifices taking their place, and the hole 259 are bounded by edges which are smoothed off at least where they join the concave face 254 of the wall 253.

The same thing applies to two other through holes 262 and 263 respectively provided on either side of the axis 202 in the wall 253 along the same median plane 261 fixed in relation to the body 203 and including the axis 202 and along respective axes 264, 265 lying in said plane 261 and intersecting the face 254, or else the reference surface 210, at points 266, 267 which are strictly symmetrical with one another in relation to the axis 202 and spaced out from one another, perpendicularly to the axis 202, by a value equal to the diameter $D_2$ of the circle 16 to be produced at the start of the incision 14 or 114.

Said holes 262 and 263 which have perpendicularly to their respective axis the same rectangular section, symmetrical in relation to the plane 261 and defined by two faces parallel therewith and two faces perpendicular thereto, and are bordered on the face 256 of the wall 253 by respective peripheral protuberances 366, 367, each of which converges towards that one of said two holes 262, 263 which corresponds thereto, enable to extend through the wall 253 a blade 268 borne by a blade carrier 269 mounted to oscillate inside the cavity 257, in relation to the body 203, to allow the orientation of an axis 270 common to the blade 268 and the blade carrier 269 and determining an own direction of these latter, in the median plane 261 fixed in relation to the body 203, either along the axis 264 or along the axis 265, passing through all the intermediate orientations. However, in the non-limiting embodiment of a keratotome according to the invention which is illustrated, these limit orientations are the only ones used to perform an incision 14 or 114 by means of the blade 268, and to this end the axis 264 is parallel with the axis 202 and offset in relation thereto by a distance corresponding to half $D_2$, while the axis 265 intersects the axis 202 opposite the face 256 of the wall 253 and is inclined in relation to the axis 202, in relation to which it diverges in the direction of the wall 253. More precisely the axis 265 forms the angle A defined with reference to FIG. 2, in relation to a plane 271 perpendicular to the axis 202.

To allow such an adjustment of orientation, the blade carrier 269 is journalled on a cap 273 rigidly connected to the body 203 in the interior thereof, around an axis 272 perpendicular both to the median plane 261 and the common axis 270 of the blade 268 and the blade carrier 269 and extending through the intersection of the axes 264 and 265, the axis 272 being thus offset both in relation to the axis 202 and the wall 253, in the direction of the interior of the cavity 257 at the level of the face 250 of the body 203. For example, the axis 272 takes the material form of attachment screws engaging coaxially in conical bearings in the blade 269, in a manner which is not shown but which can readily be imagined by a man skilled in the art, and are carried by a cap 273 of an annular ring 274 of revolution around the axis 202 which is inserted in the cavity 257 in the body 203 in a position such as to line the face 249 thereof, with interconnection, for example, by gluing or pinning.

Means 275 are also provided of any suitable kind for the adjustable pivoting of the blade carrier 269 and the blade together therewith around the axis 272 in relation to the body 203 from one to the other of its orientations corresponding with their common axis 271 coinciding with the axis 264 and the axis 265 respectively.

In the non-limiting embodiment illustrated said means 275 cooperate to this end with the blade carrier 268 via a forked member 276 received in the cavity 257 in the body 203 and comprising two arms 277, 278 which are symmetrical with one another in relation to the mean plane 261 and are situated in their own same median plane 279, perpendicular to the plane 261, inclined in relation to the axis 202 with variation of its inclination in relation thereto in dependence on the orientation of the blade carrier 269 around the axis 272 in relation to the body 203 and coinciding with the plane of FIG. 10. The two arms 277 and 278 of the member 276 are articulated on the blade carrier 269 in positions symmetrical with one another in relation to the mean direction 270 thereof, around an axis 280 lying perpendicular to the plane 261 and the axis 270, in the plane—279 i.e., parallel with the axis 272 of articulation of the blade carrier 269 in relation to the body 203, opposite from the wall 253 in relation to said axis 272, whatever the orientation of the axis 270 of the blade carrier 269 in normal conditions of use of the keratotome 200 may be—i.e., whether such orientation coincides with the axis 264 or the axis 265, or whether it is intermediate between these two limit orientations. To this end, for example, each of the arms 277, 278 bears solidly attached along the axis 280 a respective grub screw 281, 282 which engages coaxially in a respective conical bearing surface 283, 284 of the blade carrier 269, an assembly which is similar to the assembly of the articulation of the blade carrier around the axis 272 in relation to the cap 273. Of course, other articulated mountings might be adopted without exceeding the scope of the present invention.

Oppositely from their articulation around the axis 280 on the blade carrier 269, the two arms 277 and 278 are rigidly interconnected via a web 285 continuously formed with a cylindrical bore 286 of revolution around an axis 287 lying at the intersection of the planes 261 and 279 and perpendicularly intersecting the axis 280. Via the bore 286, situated approximately at the level of the orifice 258, while the axis 280 is placed closer to the axis 272 than the orifice 258, the forked member 276 receives and guides in relative rotation around the axis 287 a threaded rod 288 having between the two arms 277 and 278 of the member 276—i.e., on the same side of the web 285 as the axis 280—a head 289 via which the threaded rod 288 bears against the web 285, along the axis 287, via a washer 290. Opposite the web 285, the threaded rod 288 bears thereagainst, via a washer 291, by a nut-counternut assembly 292 which, without impeding the possible rotation of the threaded rod 288 around the axis 287 inside the bore 286, opposes any other displacement of the threaded rod 288 in relation to the member 276.

Having regard to the aforementioned orientation of the member 276, the threaded rod 288 emerges from the cavity 257 of the body 203 via its orifice 258, opposite the head 289 in relation to the web 285 of the member 276, on the side of the axis 202 opposite from its side where the axis 272 is located for articulating the blade carrier 269 to the body 203, and engages via its threads, outside the body 203, in a complementary tapped sleeve 293 articulated, around an axis 294, to a cap 295 emerging from the cavity 257 via the orifice 258 and rigidly borne by an annular ring 296 of revolution around the axis 202 and attached to the face 252 of the body 203 in the immediate vicinity of the orifice 258. The ring 296 is rigidly connected to the body 203 by any suitable means, such as screwing by means of screws radial in relation to the axis 202, and the axis 294 is orientated perpendicular to the axis 287 and the plane 261—i.e., parallel with the axes 280 and 272, in the plane 279, while the axis 294 is situated on the side of the axis 202 opposite from the side thereof on which the axis 272 is situated.

Clearly, by rotating the threaded rod 288 on itself around the axis 287 in one direction or the other inside the tapped sleeve 293, it is possible to move the axis 280 either towards or away from the axis 294, thus orientating the axis 270 of the blade carrier 269 and of the blade 268 in relation to the body 203, more particularly along the axis 264 or the axis 265. To this end the threaded rod 287 bears rigidly, but preferably adjustably, connected opposite the sleeve 293 in relation to its head 289 a roller 297 advantageously furnished jointly with the sleeve 293 with micrometric graduations of the orientation of the axis 270 of the blade 268 and the blade carrier 269 in relation to the axis 202 or in relation to the plane 271 perpendicular to the axis 202.

Preferably the limit orientations in which the axis 270 corresponds with the axis 264 and the axis 265 respectively are defined by advantageously adjustable stops.

Thus, in the embodiment illustrated, in the orientation in which the blade carrier 269 is illustrated in solid lines in FIG. 8—i.e., an orientation in which its axis 270 coincides with the axis 265—the blade carrier 269 bears against the body 203 in a zone thereof corresponding to its face 250 and substantially along the axis 287, against a screw-counterscrew assembly 388 screwed into a tapped bore 389 of the body 203, while in the orientation illustrated in chain dotted lines, in which the axis 270 coincides with the axis 264, parallel with the axis 202, the nut-counternut assembly 292 bears (in a manner not shown) against the sleeve 293, possibly via an interchangeable washer (not shown), enabling the stop to be finely adjusted.

Of course, the passage of the blade 268 and the blade carrier 269 from one to the other of the orientations 264 and 265, referring to their common axis 270, requires the blade carrier 269 to be situated totally withdrawn towards the interior of the cavity 257 in relation to the wall 253 in these two limit orientations and also in any intermediate orientation, and for the blade 268 to be also placed in this way, while the blade 268 must also be capable of being placed projecting in relation to the face 254 of the wall 253 once one of the two limit orientations is reached, to allow the incision of the cornea.

To this end the blade 268 and the blade carrier 269 have shapes which will now be described with reference to FIGS. 10 to 12 by way of non-limiting example.

Referring to FIG. 11, the blade carrier 269 has a generally oblong shape along the axis 270 and comprises two zones 298, 299 adjoining one another along said axis. In its zone 298, in which the two axes of articulation 272 and 280 lie, the blade carrier 269 has the general shape of a tubular wall of revolution around the axis 270, except for two zones strictly localized around the axes 272 and 280, in which the blade carrier 269 has external bosses receiving the grub screws representing these axes, as shown at 300 and 301 in FIG. 10 in connection with articulation around the axis 280 by means of grub screws 280 and 282, a similar mounting being used for the articulated mounting around the axis 272. In contrast, internally the blade carrier 269 has in its zone 298 a wholly cylindrical internal peripheral face 302 of revolution around the axis 270, between an open end 303 situated between the axis 280 and the orifice 258 of the body 203 in any of the afore-defined orientations of the blade carrier 269, and an end 304 taking the material form of a flat face perpendicular to the axis 271, where the zones 298 and 299 join, between the axis 272 and the wall 253 in said orientation. From the open end 303 to approximately half way between the axes 272 and 280 the tubular wall forming the zone 298 of the blade carrier 269 is formed along the plane 261, on either side of the axis 270, with two slots 305, 306 allowing the passage of a rod 307 with micrometric means 308 for adjusting the depth of incision which will be described hereinafter, while to enable the keratotome 200 to occupy as little space as possible, the tubular wall has adjacent the end 303, again in the plane 271, a bevel 307 enabling the orientation to be adopted corresponding to coincidence between the axis 270 and the axis 265, without direct contact between the blade carrier 269 and the body 203, as shown in FIG. 8. In its zone 299 the blade carrier 269 has externally a truncated shape of revolution around the axis 270 and converging towards the wall 253 in the aforementioned orientations of the blade carrier 269, with dimensions such, that whatever the orientation of the blade carrier 269 may be, it never contacts any zone of the wall 253. In said zone 299 the blade carrier 269 is formed with a flat slot 308 having a rectangular section perpendicular to the axis 270, as shown in FIG. 10. Said section is defined more particularly by two faces 309 and 310 which are parallel and symmetrical with one another in relation to a plane which is perpendicular to the plane 261, includes the axis 270 and also the axes 270 and 280, and whose outline coincides with the axis 270 as shown in FIG. 11 and with the axis 280 as shown in FIG. 10. The slot 308 is also bounded by two flat faces 311, 312 which are parallel and symmetrical with one another in relation to the plane 261, as shown in FIG. 12, where the blade carrier 269 is diagrammatically shown in chain-dot lines. If $D_6$ denotes the diameter of the face 302, the faces 311 and 312 are thus moved away from one another, perpendicular to the axis 260, by a distance $e_3$ less than $D_6$ and, for example, of the order of half $D_6$, while the faces 309 and 310 are moved apart, perpendicular to the common plane of the axes 270, 272, 280, by a distance $e_4$ less than $e_3$ and, for example, of the order of half $e_3$, so that more particularly the end face 304 boarders the slot 308 in all directions, as shown in FIG. 10.

Corresponding to this conformation of the blade carrier 269, the blade 268 takes the general form of a flat blade 313 having perpendicular to the axis 270 a running section substantially identical with that of the slot 308, so that the latter can guide the blade 313 in relative sliding along the axis 270, to the exclusion of any other possible relative movement, by the sliding contact of the faces 309 to 312 with respective flat faces of the blade 313—i.e., respectively faces 314 and 315 which are parallel and symmetrical with one another in relation to the common plane of the axes 270, 272 and 280, and faces 335 and 336 parallel and symmetrical with one another in relation to the plane 261. The blade 313 uniformly has such a section between two ends 317 and 318 turned towards the wall 253 and the orifice 258 respectively in any of the aforementioned common orientations of the blade carrier 269 and the blade 268. Towards its end 317 the blade 313 bears rigidly connected a cutting tip, for example a diamond cutting tip 319 which, in the embodiment illustrated, takes the form of a lancet symmetrical in relation to the common plane of the axes 270, 272 and 280 and in relation to the plane 261, and terminating in a sharp point 320 in the direction of the wall 253, it being understood that any other form of cutting tip might be selected without exceeding the scope of the present invention. Via its end 318 the blade 313 is rigidly connected to a piston 321 having a general shape of revolution around the axis 270, defined by a cylindrical peripheral face 322 of revolution around the axis 270 with a diameter substantially equal to $D_6$, so as to establish a sliding contact for mutual sliding guidance along the axis 270 between said face 322 of the piston 321 and the face 302 of the blade carrier 269; the piston 321 is moreover bounded by two flat faces perpendicular to the axis 270, namely one face 323 situated opposite the end face 304, and one face 325 turned in the opposite direction—i.e., towards the orifice 258 of the body 203 in the orientations of the axis 270 defined hereinbefore.

The blade 268 and the blade carrier 269 are so dimensioned, in a manner readily understood by a man skilled in the art, that the blade 268 can more particularly occupy an inoperative position (illustrated in solid lines in FIG. 11)—i.e., a position in which the blade 313 is engaged, by a zone adjacent its end 317, in the slot 308 inside which the cutting tip 319 however remains totally retracted, while the piston 321 disposed inside the zone 298 of the blade carrier 269 with mutual contact between the faces 322 and 302 is separated from the end 303 by its face 324 by a distance $D_7$ close to $D_6$, while it is separated from the end face 304 by its face 323 by a distance $D_8$ considerably greater than $D_7$; said distance $D_8$ is such that the blade 268 can be displaced, by sliding along the axis 270 in relation to the blade carrier 269, into a cutting position (shown in chain-dot lines in FIG. 11) in which, after the piston 321 has been moved close to the end face 304, the cutting tip 319 forms a projection not only out of the blade carrier 269, but also out of the body 203, through the wall 253 via one of the holes 262 and 263, in dependence on whether the axis 270 coincides with the axis 264 or the axis 265, to be thus placed projecting in relation to the face 254 of the wall 253—i.e., in relation to the reference surface 210—, to penetrate into a cornea 2 whose surface 18 fits onto the face 254 and to thus incise said cornea. It should be noted that if the axis 270 coincides with the axis 264, the incision is made parallel with the axis 202—i.e., in the form of a cylinder of revolution around the axis 202, when the body 203 is rotated inside the support 201 by taking action on the entraining means 232, while if the axis 270 coincides with the axis 265, the cutting tip 319 diverges in relation to the axis 202 in a direction 325 of the axis 270 moving from the end 318 of the blade 313 towards its end 317, so that when the body 203 rotates around the axis 202 in relation to the support 201, the cutting tip 319 makes a truncated incision, diverging starting from the surface 18 of the cornea coinciding with the reference surface 210. However, because of the positioning of the axes 264 and 265 defined hereinbefore, the cylindrical incision and the truncated incision thus performed maintain the same diameter equal to $D_2$ at the level of the reference surface 210—i.e., at the level of the surface 18 of the cornea e.

The aforementioned means 308 for adjusting the depth of incision are used to move the blade 268 as required into its cutting position, projecting in relation to the face 254 of the wall 253 or in relation to the reference surface 210, or in contrast to move the blade 268 into its inoperative position, in which its tip 308 is withdrawn inside the blade carrier 269 and in relation to the wall 253. The means 308 can take any form appropriate for this purpose.

In the non-limiting embodiment illustrated, the retracting movement is automatically produced by a helical spring 326 operating under compression between the face 323 of the piston 321 and the end face 304 of the blade carrier 269, around the blade 313, but retracted towards the axis 270 in relation to the face 302 of the blade carrier 269, as shown in FIGS. 10 and 11.

The means 308 for adjusting the depth of incision are in that case formed by single-acting means applying to the piston 321 via its face 324 a thrust opposing that of the spring 326, although it must be understood that it would not exceed the scope of the present invention to use double-acting means for adjusting the depth of incision, more particularly in the absence of a spring 326, to positively control not only the movement of the blade 268 into its cutting position, but also its movement into the inoperative position, or any other means allowing, by a translation movement of the blade 268 along the axis 270 in relation to the blade carrier 260, the formation of a controlled projection of the cutting tip 308 in relation to the face 254 of the wall 253 and in relation to the reference surface 210.

In the embodiment illustrated the means 308 for adjusting the depth of incision 308 are of a micrometric nature and comprise a sleeve 327 formed along its own axis 328 with a tapped bore 331 and mounted to pivot, in relation to the body 303, around an axis 329 on a cap 330 rigidly connected with the body 203 in a position opposite from that of the cap 295 in relation to the axis 202. The cap 330 forms a projection out of the body 203 via its orifice 258 so that the axis 329 is situated substantially in the same plan (not shown), perpendicular to the axis 202 as the axis 295, with which the axis 329 is parallel, so that when the sleeve 327 pivots around the axis 329 in relation to the cap 330, its axis 328 remains permanently in the plane 261. Moreover, the axis 329 is disposed so that the axis 280 is situated in relation thereto substantially at the same distance when the axis 270 of the blade 260 and of the blade carrier 269 coincides with the axis 264 or coincides with the axis 265.

The aforementioned rectilinear rod 307 extends coaxially and continuously through the sleeve 327 and cooperates with the tapping of its bore 331 via a threading which is complementary therewith, so that a rotation of the rod 307 around the axis 328 in relation to the sleeve 327 causes a relative translation movement parallel with the axis 328.

Such a relative rotation can be produced as required by means of a roller 332 which the rod 307 bears rigidly connected but advantageously adjustable along the axis 328 on one side of the sleeve 327, as was stated hereinbefore with regard to the roller 297 and the threaded rod 288 of the means 275 for adjusting the orientation of the blade carrier 269 and the blade 268; just like the roller 297 and the sleeve 293 with which the rod 288 cooperates, the roller 332 and the sleeve 327 jointly bear micrometric graduations 333. These graduations 333, advantageously expressed in depth of incision—i.e., in the value of the projection formed by the cutting tip 308 of the blade 268, along its own direction 270, in relation to the face 254 of the wall 253 and in relation to the reference surface 210—are preferably sub-divided on the sleeve 327 into two zones which can readily be distinguished from one another, for example, by a selection of different colours, and which correspond to the graduations which can be used when the axis 270 of the blade 268 and the blade carrier 269 coincide with the axis 264 and the axis 265 respectively.

Of course, the roller 332 of the means 308 for adjusting the depth of incision is disposed outside the body 203 into which the rod 307 enters, opposite from the sleeve 327 in relation to the roller 332, via the orifice 258 to cooperate with the piston 321 of the blade 268 inside the blade carrier 269.

To this end the rod 307 bears rigidly connected at its end opposite its end bearing the roller 332 in relation to the sleeve 327, a spherical ball 334 having a diameter substantially equal to $D_6$ and engaging inside the zone 298 of the blade carrier 269 bearing against the face 324 of the piston 321 and in contact with the face 302, so as to be guided by the latter in relative translation movement along the axis 270, to the exclusion of any other possible relative displacement. Stop means, which are not shown but can easily be imagined by a man skilled in the art, can be provided to prevent the ball 334 from escaping out of the zone 298 of the blade carrier 269 by the end 303, although such means are not indispensable.

Of course, for the rod 307 to apply to the piston 321 via its ball 334 a thrust opposing that of the spring 326, whatever the orientation of the axis 270 may be—i.e., whether it is oriented along the axis 264 or the axis 265 or in an intermediate orientation—the axis 329 is placed far enough away from the axis 272 for the rod 307, via its axis 328, and the blade 268-blade carrier 269 assembly, by its axis 270, to permanently form therebetween an angle C much larger than 90°, both in the two limit orientations of coincidence with the axes 264 and 265 and in the intermediate orientations between said two limit orientations during passage from one to the other; in the non-limiting embodiment illustrated, the value of the angle C is of the order of 140° in the two limit orientations and varies between that value and 180° during the passage from one to the other of the limit orientations. The rod 307 therefore always applies a thrust in the direction 325 by the pivot 334 to the blade 268.

The operation of the keratotome 200 just disclosed will now be described with reference to the making of an incision of the kind illustrated at 114 in FIG. 5.

In an initial state of the keratotome 200 the blade 268 is placed in the inoperative position and the blade 268-blade carrier 269 assembly is placed in an orientation such that its axis 270 coincides with the axis 265, as shown in chain-dot lines in FIG. 8, by a suitable positioning of the rollers 332 and 297.

Taking as his guide the hole 259, the surgeon then places the keratotome 200 by its base portion 204 on the surface 18 of the cornea 2 to be incised, placing the axis 202 to coincide with the visual axis. The suction means 211 are then started to put the cavity 206 under negative pressure and thus on the one hand to immobilize the support 201 on the cornea bearing against the bearing surfaces 208 and 209 and, on the other hand and because of such bearing, to give to the surface 18 of the cornea 2 a shape coinciding with the reference surface 210—i.e., a form such that it fits onto, but without mutual contact pressure, the face 254 of the wall 253.

Then, by acting on the roller 332 while maintaining the coincidence between the axis 270 and the axis 264, the blade 268 is moved into a cutting position such that by its cutting tip 319 projects from the face 254 of the wall 253 and in relation to the reference surface 210. During its passage into this position, the cutting tip 319 enters the cornea 2 by a selected depth adjusted by reading off the graduation 333 and, for example, directly equal to $e_2$, i.e., of the order of 50 μm.

Then, by acting on the button 244 or by means of the motor taking its place, the surgeon rotates the body 203 around the axis 202 in relation to the support 201 through at least 360° to form the cylindrical zone 115 of the incision 114 to be made.

Then, after stopping the rotation of the body 203 in relation to the support 201, and by acting on the roller 332, the surgeon returns the blade 268 to its inoperative position—i.e., withdraws the blade inside the blade carrier 269—then, by acting on the roller 297, moves the axis 270 of the latter and of the blade 268 into coincidence with the axis 265.

By acting again on the roller 332, the surgeon then brings the blade 286 out of the blade carrier 269 and, causing it to pass through the wall 253 via the hole 263, moves the blade 268 into projection along the axis 265 in relation to the face 254 and the reference surface 210, doing so by a value which he adjusts by reading off the graduation 333; it will be noted that during this movement the cutting tip 319 returns to the inside of the already produced zone 315 of the incision 114 to be made.

Then, by acting manually on the button 244 or putting into operation the motor taking its place, the surgeon again rotates the body 203 around the axis 202 in relation to the support 201 through at least 360°, this forming a portion of the zone 117 directly adjacent the zone 115 of the incision 114 to be made.

Then, by again acting on the roller 332 without acting on the roller 297, after stopping the rotation, the surgeon increases the value of the projection of the cutting tip 319 in relation to the face 254 of the wall 253 and in relation to the reference surface 210, this causing the cutting tip 319 to penetrate deeper into the cornea 2, whereafter he again rotates the body 203 around the axis 202 in relation to the support 201 through at least 360° to form a fresh portion of the zone 117 of the incision 114. These operations are repeated until the whole of the zone 117, as far as the circle 17, is thus produced.

Then, by acting on the roller 332, after stopping the rotation, the surgeon returns the blade 268 into the inoperative position, stops the suction means 211, cancels out the vacuum in the cavity 206 to release the connection between the keratotome 200 and the cornea 2, and finally removes the keratotome 200. The lense 107 can then be put in place as indicated hereinbefore.

When an incision 14 of the kind illustrated in FIG. 2 must be made, it is possible to use only the orientation of the blade carrier 269 and the blade 268 corresponding to the coincidence of the axes 270 and 265, in a manner which can readily be deduced from what has just been described. However, a greater precision is obtained in the conformation of the incision by nevertheless starting the incision by orientating the axis 270 along the axis 264, as was described hereinbefore, to first incise the cornea cylindrically over 360° to a depth which can be much less than the value of 50 $\mu$m indicated hereinbefore—i.e., which can remain negligible in relation to the other dimensions of the incision, while facilitating the initial penetration of the cutting tip 319 in the cornea 2 and thus ensuring perfect circularity for the circle 16 via which the incision 14 emerges at the surface 18 of the cornea 2. The value of the dimension $e_2$, as regards more particularly the face 103 of the lense 101 (FIGS. 5, 6, 7) and the zone 115 of the incision 114 (FIG. 5), is essentially dictated by such a wish for precision of the incision and can therefore remain much smaller than the dimension, parallel with the visual axis, of the incisions made in the cornea to receive the lenses hitherto used in keratometry.

Clearly, the embodiment of the keratotome 200 according to the invention just described forms only a non-limiting example to which the man skilled in the art can made numerous variants without exceeding the scope of the present invention, more particularly with the object to enabling the blade and the blade carrier to be positioned not only in two predetermined limit orientations, but also in any other optionally selected intermediate orientation, while maintaining an identity of positioning, in relation to the axis 202 of rotation of the body 203 in relation to the support 201, of the intersection of the cutting tip 319 with the reference surface 210—i.e., with the face 254 of the wall 253, if reference is made to the embodiment illustrated.

What is claimed is:

1. A lense for keratometry, comprising:
   (a) an optical zone which has a lenticular shape with predetermined optical axis and is bounded by a convex front face and a concave rear face whose respective geometries are determined relative to application of said rear face zone closely in a close fit against a cornea, and relative to predetermined optical characteristics; and
   (b) an anchoring zone having an annular shape of revolution around the optical axis and edging the optical zone in a direction away from the optical axis for insertion into an annular incision in the cornea;
   (c) wherein the anchoring zone is disposed rearwardly of the front face of the optical zone and projects outwardly from the rear face of the optical zone, and the anchoring zone is bounded by a front face and a rear face which are respectively connected to the front face and rear face of the optical zone and converge in a direction away from the optical axis so as to produce a progressive thinning of the anchoring zone from the optical zone to a peripheral edge of the lense, the front face and the rear face of the anchoring zone having substantially the same shape and the same dimensions when they are viewed in section along any half-plane bounded by the optical axis.

2. A lense according to claim 1, wherein the front face of the anchoring zone has an inclination substantially less than 90° with respect to a plane perpendicular to the optical axis.

3. A lense according to claim 2, wherein the rear face of the anchoring zone has an inclination of between about 40° and about 45°, and the front face of the anchoring zone has an inclination of between about 50° and about 55°, with respect to said plane perpendicular to the optical axis.

4. A lense according to claim 3, wherein the rear face of the anchoring zone has an inclination of 42° with respect to said plane perpendicular to the optical axis.

5. A lense according to claim 1, which comprises at least one flexible and biocompatible polymer selected from the group consisting of natural polymers and synthetic polymers.

6. A lense according to claim 1, wherein the front face and rear face of the anchoring zone are substantially truncated faces of revolution around the optical axis.

7. A lense according to claim 1, wherein the front face and rear face of the anchoring zone join one another at the peripheral edge of the lense in a circular edge.

8. A lense according to claim 1, wherein the front face and rear face of the anchoring zone are connected to one another at the peripheral edge of the lense via a peripheral face of revolution around the optical axis.

9. A lense according to claim 8, wherein the peripheral face is a cylindrical face of revolution around the optical axis.

10. A lense according to claim 1, wherein the front face of the optical zone has the shape of a spherical cap centered on the optical axis.

11. A lense according to claim 1, wherein the rear face of the anchoring zone is directly connected to the rear face of the optical zone.

12. A lense according to claim 1, wherein the front face of the anchoring zone is connected to the rear face of the optical zone via a peripheral discontinuity thereof of revolution around the optical axis.

13. A lense according to claim 12, wherein the peripheral discontinuity is a cylindrical one of revolution around the optical axis.

14. A lense according to claim 1, wherein the rear face of the optical zone has the shape of a spherical cap centered on the optical axis.

15. A lense according to claim 1, wherein the rear face of the optical zone has a non-spherical shape.

16. A lense according to claim 15, having a point of reference in angular orientation around the optical axis.

17. A lense according to claim 1, wherein the front face of the anchoring zone is directly connected to the front fact of the optical zone.

18. A lense according to claim 1, wherein the rear face of the anchoring zone is connected to the rear face of the optical zone via a peripheral shoulder of revolution around the optical axis.

19. A lense according to claim 18, wherein the peripheral shoulder is a cylindrical shoulder of revolution around the optical axis.

20. A lense according to claim 1, wherein the anchoring zone has at least one notch opening into the peripheral edge of the lense and in zones of the front face and rear face of the anchoring zone close to the peripheral edge of the lense.

* * * * *